US006620778B2

(12) United States Patent
Mallee et al.

(10) Patent No.: US 6,620,778 B2
(45) Date of Patent: Sep. 16, 2003

(54) CYSTEINE/GLYCINE RICH PEPTIDES

(75) Inventors: Leon Franciscus Mallee, Utrecht (NL);
Ram Nimmagudda, Oneonta, NY (US); Johannes Wilhelmus L. Boumans, Ouderker Aan de Amstel (NL)

(73) Assignee: Campina Melkunie B.V., Zaltbommel (NL)

( * ) Notice: Subject to any disclaimer, the term of this patent is extended or adjusted under 35 U.S.C. 154(b) by 0 days.

(21) Appl. No.: 09/983,237

(22) Filed: Oct. 23, 2001

(65) Prior Publication Data

US 2002/0090670 A1 Jul. 11, 2002

(30) Foreign Application Priority Data

Oct. 24, 2000 (EP) ............................................. 00203699

(51) Int. Cl.$^7$ ........................ A61K 38/00; A01N 37/18
(52) U.S. Cl. ............................. 514/2; 514/12; 530/300; 530/362; 530/365; 530/366; 530/367; 530/370; 530/833; 435/23; 435/24; 435/113
(58) Field of Search ................................ 530/300, 362, 530/365, 366, 367, 370, 833; 435/23, 24, 113; 514/2, 21

(56) References Cited

U.S. PATENT DOCUMENTS

| 5,451,412 A | 9/1995 | Bounous et al. |
| 5,464,825 A | 11/1995 | Anderson et al. |
| 5,821,224 A | * 10/1998 | Selsted et al. ................. 514/12 |
| 5,962,254 A | 10/1999 | Saniez et al. |

FOREIGN PATENT DOCUMENTS

| DE | 41 30 284 A1 | 3/1993 |
| EP | 0 665 012 A1 | 8/1995 |
| WO | WO 98/44807 | 10/1998 |

OTHER PUBLICATIONS

Duvick et al., Purification and Characterization of a Novel Antimicrobial Peptide from Maize (zea mays L.) Kernels. J. Biol. Chem. 267, 18814–18820 (1992).*

* cited by examiner

Primary Examiner—Christopher S. F. Low
Assistant Examiner—Chih-Min Kam
(74) Attorney, Agent, or Firm—Oblon, Spivak, McClelland, Maier & Neustadt, P.C.

(57) ABSTRACT

Described is a method for the preparation of a mixture of peptides having a cysteine content between 7–20 w/w % from a protein source, comprising cysteine containing proteins, comprising the steps of:
a) cleaving the proteins of the protein source into peptides;
b) digesting the peptides obtained in step a) by an exopeptidase, the action of which is at least attenuated at the position of a cysteine in the peptide, therewith forming digested peptides having a terminal cysteine;
c) purifying the digested peptides,
and the use of the preparation as active component in a medicament, especially for the treatment of conditions mediated by oxidative damage and for the elevation of cellular glutathion levels in the human or animal body.

62 Claims, 1 Drawing Sheet

CYSTEINE/GLYCINE RICH PEPTIDES

FIELD OF THE INVENTION

The invention relates to a method for the preparation of a mixture of peptides having a cysteine- or cysteine/glycine content between 7–20 w/w %, to preparations comprising said peptides and to the use of such preparations as active compound in a medicament.

Peptides are herein defined as amino acid chains, derived from a protein; the molecular weight of the peptides is preferably between 200D and 8000D, more preferably between 1000D and 5000D.

BACKGROUND OF THE INVENTION

In the art, there is a great demand for cysteine and cysteine/glycine comprising compounds for effective administration of said amino acids to the human or animal body. The availability of especially cysteine and to a lesser extent glycine, is a limiting factor in the syntheses of glutathion. Proper administration of cysteine, but also of glycine is therefore demanded in cases where an elevation of cellular glutathion levels in the human or animal body are needed.

Glutathion (GSH) is a tripeptide-thiol (L-γ-glutamyl-L-cysteinylglycine) having a broad range of vital functions, including protection of cells against oxygen intermediates, free radicals, by products of the oxygen requiring metabolism, and detoxification of xenobiotics. Further, glutathion seems to play a role in the prevention of cataract and oxidative DNA injury. Glutathion is therefore regarded as an important compound against oxidative stress related diseases like myocardial ischemia, cancer and cataract.

In view of the crucial role played by glutathion either in combatting the assaults of free radical injuries or in detoxification of xenobiotics, inclusing drug metabolites (such as cyclophosphamide, paraquat and acetaminophen) and in preventing peroxidation of cell components, a method for maintaining hepatic stores of glutathion, particularly during times of stress to the body, including chemotherapy, is needed.

In the art, various methods are known to increase cellular levels of glutathion. Administration to animals of the glutathion amino acid precursors glutamic acid, cysteine and glycine, may produce an increase in cellular glutathion, but there is a limit to the effectiveness of this procedure.

Cellular concentrations of GSH are dependent on the supply of cysteine, which is often the limiting amino acid, and which is derived from dietary protein and also by trans-sulfuration from methionine in the liver. However, administration of cysteine as free amino acid is not an ideal way to increase GSH concentrations because cysteine is rapidly metabolised and furthermore, appears to be toxic to cells at higher concentrations. Administration to animals of compounds that are transported into cells and converted intracellularly into cysteine is sometimes useful in increasing cellular glutathion levels.

Another way in which tissue GSH concentration may be increased is by administration of gamma glutamylcysteine or of gamma-glutamylcystine. The administered gamma-glutamyl amino acid is transported intact and serves as a substrate of GSH synthetase. It is also known that administration of N-acetyl-L-cysteine can often increase tissue concentrations of GSH. Other reports on using N-mercaptopropionyl glycine for increasing intracellular glutathion are known. A few clinical trials have been done using mercaptopropionyl glycine to elevate intracellular glutathion.

That the administration of glutathion itself might lead to increased glutathion levels has also been considered. However, there is no published evidence that shows that intact glutathion enters cells. In fact, there are several reports on particular biological systems indicating that glutathion itself is not transported into cells. The increase in cellular glutathion sometimes found after administration of glutathion is due to (a) extracellular breakdown of glutathion, (b) transport into cells of free amino acids or dipeptides derived from glutathion extracellularly, and (c) intracellular resynthesis of glutathion.

Apart from these conventional methods for increasing glutathion levels, there have been several attempts to demonstrate how glutathion can be enhanced intracellularly. All these relate to synthetic derivatives or about intact undenatured proteins which are heat labile and none whatsoever to natural derived peptide mixtures. Some of the relevant ones are summarised below:

U.S. Pat. No. 5,869,456 relates to preparation of pure alkyl esters of glutathion (95% pure) and a method for increasing intracellular glutathion levels by administering such alkyl diester of glutathion.

U.S. Pat. No. 5,464,825 describes the method for preparation and use of N-acyl glutathion monoalkyl esters to provide increased intracellular levels of glutathion or glutathion equivalents, e.g. N-acyl glutathion or glutathion monoalkyl esters.

U.S. Pat. No. 5,248,697 describes a method for maintaining and/or enhancing tissue or plasma levels of glutathion. The patent teaches the art of treatment of a mammal with a supranormal amount of glutamine, or a glutamine equivalent, to prevent the reduction in tissue glutathion levels associated with exposure of the mammal to a compound capable of oxidative injury to the tissue.

U.S. Pat. No. 4,665,082 discusses the role of L-2-oxothiazolidine-4-carboxylate, a sulfur analog of 5-oxoproline, cleaved by the enzyme-5-oxo-L-prolinase to form cysteine, thus providing the basis for a cysteine delivery system by the addition of L-2-oxothiazolidine-4-carboxylate to base amino acid solutions or by injecting it directly into in vivo cells.

DE patent No 4,329,857 teaches the use of thiol compounds (cysteine and its derivatives or analogues like N-acetyl cysteine, homocysteine, glutathion, 2-oxothiazolidine-4-carboxylic acid) as an agent for strengthening the immune system and immune reactions.

SUMMARY OF THE INVENTION

According to the present invention, a novel method for the preparation of a mixture of peptides having a cysteine content between 7–20 w/w % from a protein source, comprising cysteine containing proteins is provided. The protein source is preferably a natural protein source. The peptide mixture prepared according to this embodiment of the present invention has the advantage that it is derived from natural protein sources and will not show any adverse side-effects, whereas chemically produced cystein derivatives as mentioned in the prior art, have shown adverse side effects. There has been found that such a preparation of a peptide mixture can be very advantageously used as cysteine source in diet supplements or in medicaments, as will be explained below.

The method is characterized in that it comprises the steps of:
- a) cleaving the proteins of the protein source into peptides;
- b) digesting the peptides obtained in step a) by at least one exopeptidase, the action of which is at least attenuated at the position of a cysteine in the peptide, therewith forming digested peptides having a terminal cysteine;
- c) purifying the digested peptides.

In the first step a) proteins of the protein source are cleaved into smaller peptides. This cleavage can be performed by cleavage reactions, known in the art; preferably, the cleavage is performed by enzymatic hydrolysis of the peptide bonds of the protein by e.g. an endopeptidase, resulting in the peptides of about the desired length, and therewith increasing the amount of substrate for the exopeptidase. In a second step, the peptides as obtained by the cleavage reaction, are digested by at least one exopeptidase. With "at least one exopeptidase" is meant that the digestion reaction can be carried out by one or more different exopeptidases. Exopeptidases release amino acids from the terminal ends of the peptides one by one. The exopeptidase and the digestion reaction conditions are chosen such, that the exopeptidase action is at least attenuated at the position of a cysteine in the peptide. With "at least attenuated" is meant that the exopeptidase does not remove the cysteine from the peptide at the chosen reaction conditions or has very low preference for the cleavage of cysteine, therewith rendering said cleavage reaction very slow compared to cleavage of other amino acids from the peptide. By the use of such an exopeptidase and condition, the peptides are generated of which the terminal amino acids have been removed up to the cysteine residue most close to said terminus. The skilled person will be able to find conditions at which commercially available enzymes with exopeptidase function having attenuated action at the cysteine. It is to be understood that the peptides may have one or more amino acid chains that are coupled to each other by disulfide bridges of cysteine residues, present in the said amino acid chains. "A digested peptide having a terminal cysteine" therefore reflects to the fact that at least one of the termini of such a multi-chain peptide has a terminal cysteine. Of course, such a peptide may contain more than one terminal cysteine. Preferably, the enzymatic activity is inactivated before the purification step, e.g. by a pH shift or a thermal heat inactivation treatment.

Preferably, the exopeptidase comprises Carboxypeptidase Y (E.C.3.4.16.1.), as it has been found that this enzyme can be very effectively attenuated at cysteine residues, therewith producing peptides with terminal cysteine residues.

The cleavage step a) and the digestion step b) can be conducted simultaneously, e.g. by using an endopeptidase and an exopeptidase that both function at the same reaction conditions. Also, enzyme preparations can be used that have both endopeptidase and exopeptidase activity.

Finally, these digested peptides are purified. Suitable methods to purify the digested peptides from free amino acids, released by the exopeptidase, are known in the art. Since a difference in molecular weight is created between the cystine and glycine containing peptides and the other free amino acids, the cystine and glycine peptides can be purified using this difference. Several techniques, known in the art, could be used. Preferably the free amino acids are separated using a membrane process, preferably ultra or nanofiltration. The purification step can also advantageously comprise the use of an immobilized metal affinity chromatography step (IMAC) accordingly to Kronina et al., Journal of Chromatography A, 852 (1999) pp 261–272. The cysteine and glycine rich peptides can hereafter be dried.

In a special embodiment, the exopeptidase in step b) and the cleavage reaction are chosen such, that the exopeptidase is at least attenuated both at the position of a cysteine as well as of glycine in the peptide. This will result in digested peptides having predominantly a terminal cysteine or glycine.

The purified peptides, either enriched in cysteine residues or enriched in both cysteine and glycine residues, have shown to be very suitable sources for these limiting amino acids to be readily administered, in order to elevate the cysteine and glycine rates in the human or animal body, and may therefore elevate the intracellular glutathion levels.

The protein source may be any source as long as it comprises cysteine-containing proteins. In case a cysteine and glycine rich peptide preparation is to be produced, the protein source should contain proteins that contain glycine and cysteine.

Preferably, the protein source comprises at least two different proteins, that both contribute to the glycine and/or cysteine content of the peptides. One of the proteins may be glycine rich, whereas the second protein may be cystein rich. The protein source can also be prepared before being subjected to the method of the present invention, by e.g. two or more protein sources before or during the cleavage step.

Preferably, the protein source consists of edible proteins, so that the digested peptides can be used as food additive. In a very special embodiment, the protein source comprises whey protein isolates (WPI) and/or whey protein concentrates (WPC). The terms "whey protein isolates" and "whey protein concentrates" are known in the field. Whey protein cincentrate is a whey protein product having 35–80 w/w % protein, whereas whey protein isolate has a protein content of 90 w/w % or higher. An example of WPC is Esprion 580 from DMV International; an example of WPI is Bipro from Bio-isolates Ltd. Whey protein is an important cysteine source and it is thought that whey protein concentrate induces glutathion production in animal organs, see e.g. U.S. Pat. No. 5,451,412. However, whey protein concentrates as such are not as suitable for the elevation of the intracellular glutathion levels compared to the peptides according to the present invention. The concentration of cystein and glycine in the intact whey proteins is much lower than in the peptides of the invention, and therefore requires much higher doses of the intact whey protein to reach an acceptable level of cystein in the application.

A further disadvantage of U.S. Pat. No. 5,451,412 is that the use of totally undenatured whey protein products can be very costly since it requires very delicate process conditions. Whey protein isolate comprises very suitable cysteine and glycine rich proteins, such as albumin, especially αlactalbumin and bovine serum albumin. Said proteins are advantageously used in or as starting protein source of the method according to the invention.

In another preferred embodiment, the protein source comprises one or more of the group consisting of albumine, especially α-lactalbumin, bovine serum albumin, egg proteins (e.g. ovalbumin, cystatin) wheat gluten, maize protein isolate.

Preferably, steps a) and b) are done at conditions, wherein sulfur bridges between cysteine residues as present in the proteins in the protein source are kept in the oxidised form as much as possible. In this way, cysteine-rich peptide mixtures are obtained, in which most of the cystein residues are oxidised and coupled to other peptides through disulfide bridges. Although the correct nomenclature for cysteins in oxidized form (i.e. being coupled to another cysteine residu by a sulfur bridge) is "cystine", in this application "cysteine"

is defined both as cysteine in the reduced form (having free SH-groups) as in the oxidized (cystine) form. Peptides, wherein the sulfur bridges between the cysteine residues are intact, may mimick parts of the native original protein from which the peptides are derived, therewith possibly conferring an improved biologic action compared to that of the separate peptides in reduced form. Further, the oxidized form is less reactive and therefor more stable in applications that undergo a heat treatment like pasteurization or sterilization.

A further advantage is the fact that many enzymes having exopeptidase activity do not cleave oxidized cysteines, whereas cysteines in reduced form may be cleaved by said enzymes from the peptides, although with a relative low activity. In order to produce peptide mixtures in native, i.e. undenatured form, steps a) and b) are preferably done at a pH between 2 and 8.

It is preferred to carry out the hydrolytic processes in acidic environments. At acid pH the disulfide bridges in cystine are more stable than at basic pH. [Creighton, T. E., 1993, Proteins: structures and Molecular Properties. $2^{nd}$ Ed.; Freeman and Company, New York ]

It is preferred to cleave the proteins of the protein source in step a) by an enzyme with endopeptidase function. Using such an enzyme makes it possible to cleave the proteins under undenaturing (i.e. native) conditions, resulting in undenatured cleavage products. Physical or chemical cleavage mostly implicates application of denaturing conditions that can not be used if intact native peptide mixtures are to be obtained. For this, the expopeptidase digestion should also preferably take place at undenaturing conditions. The skilled person will know the proper conditions to yield intact native peptide mixtures. "Intact native peptide" is in this content to be understood as a peptide, having the same conformation as the said peptide has in the native, functional protein.

In a very attractive embodiment, the enzyme with endopeptidase function also has exopeptidase function, the exopeptidase function of which is attenuated at the position of cysteine or both at glycine and cysteine. Such enzymes are known in the art and the advantage thereof is that steps a) and b) can be done simultaneously. Examples of preferred enzymes having both endopeptidase as exopeptidase functions are Flavourzyme, Acid Protease A, Protease M, Protease 2A, Protease B, Corolase PN-L, Acid Protease or a combination of one or more thereof.

The invention further relates to preparations comprising cysteine-rich peptides, comprising 7–20 w/w % cysteine and to such a preparation comprising 7–20 w/w % of cysteine/glycine. As indicated above, said preparations can advantageously be used for administration to animals or humans in order to effectively improve the cysteine uptake of cysteine or a combination of cysteine and glycine for e.g. elevation of the intracellular glutathion level. Preferably, at least 80% of the peptides of the preparation comprises terminal cysteines and/or glycines, which are then readily available for the human or animal body. These terminal cysteines and/or glycines are obtained by the use of the exopeptidase as discussed above.

Further, the invention relates to the use of a preparation according to the invention as active compound in a medicament, especially in a medicament for treatment of conditions mediated by oxidative damage and in a medicament for the elevation of cellular glutathion levels in the human or animal body. For this, the preparation can be combined with any suitable carrier, diluent adjuvant etc. in order to obtain the medicament in the desired administration form. The preparation can also advantageously be used in an infant formula, e.g. in a breast milk substitute.

The invention is now illustrated in the following examples and figures which are meant to be illustrative only and not to limit the scope of the invention.

BRIEF DESCRIPTION OF THE DRAWINGS

FIG. 1b shows a fluorescence spectrum with an excitation wavelength of 386 nm and an emission wavelength of 514 nm of the hydrolysate of FIG. 1a.

EXAMPLE 1

Figure 1A:
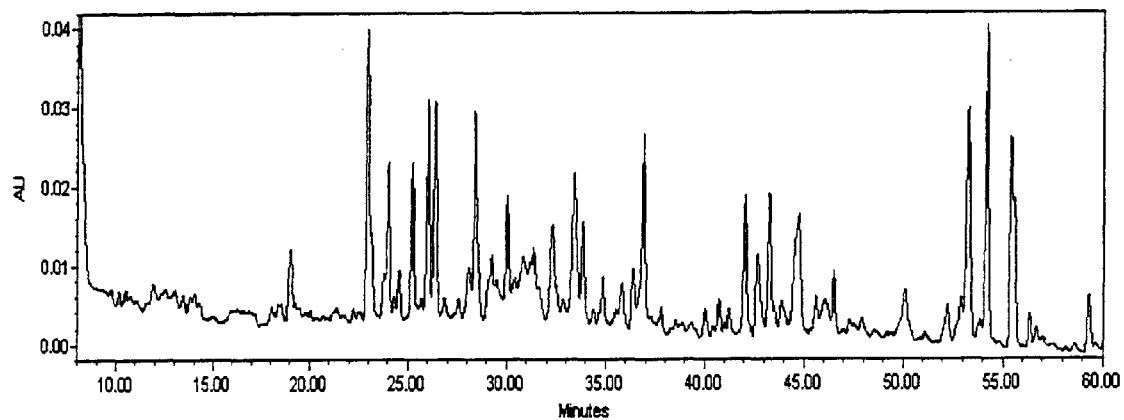
FIG. 1a shows an absorption spectrum at 214 nm of a hydrolysate according to the invention.

A 10% whey protein isolate (WPI) solution is prepared and then hydrolysed using enzymes. Several combinations of enzymes were used (Table 1).

TABLE 1

| | Enzyme(s) used | |
|---|---|---|
| Exp No | Enzyme 1 | Enzyme 2 |
| A | Pepsin (Merck) 0.5% | Protease M (Amano) 0.5% |
| B | Pepsin (Merck) 0.75% | Corolase LAP (Rohm) 2% |
| C | Pepsin (Merck) 0.5% | Acid Protease (EDC) 0.5% |
| D | Flavourzyme (Novo) 1% | |
| E | Acid Protease (EDC) 1% | |

Solutions 1–3 were first hydrolysed with pepsin for 6 hours at pH 2.0. Hereafter, the pH was increased to 7.0 using sodium hydroxide. The second enzyme was added and solutions incubated for 20 hours. The solutions containing a single enzyme were hydrolysed for 20 hours at 50° C. at pH 7 and 3 for respectively Flavourzyme and Acid Protease.

Hydrolytic reaction was stopped by heating the solutions to 85° C. for 15 minutes. Hereafter, the free amino acids were removed from the peptides containing cysteine using ultrafiltration. A membrane with a nominal molecular weight (NMW) cut off of 1000 dalton was used. The solutions were ultrafiltered to 500% diafiltration.

Protein was measured using the Kjeldahl method. Cysteine concentration was measured using the Ellmann's reagents. [Beveridge et al (1974) Journal of Food Science Volume 39, p. 49–51] The peptides were then freeze dried.

The table below lists the concentrations of both cystine and glycine in the whey protein isolate and peptides.

| | Total Cystine on protein | Total Glycine on protein |
|---|---|---|
| WPI | 3.3% | 1.9% |
| 1 | 8.5% | 2.4% |
| 2 | 11.9% | 2.7% |
| 3 | 12.4% | 2.7% |
| 4 | 9.7% | 2.1% |
| 5 | 10.9% | 3.0% |

EXAMPLE 2

A 10% whey protein concentrate containing 80% protein solution is prepared and then hydrolysed using 1% Acid Protease from Enzyme Development Corporation. The solution was hydrolysed for 20 hours at pH 3.0. The reaction was stopped by heating the solution to 90° C. for 10 minutes. Hereafter, the solution was ultrafiltered using a membrane having a NMW cut off of 1000 dalton.

Cysteine concentration was measured as a function of the %-diafiltration (table 2).

TABLE 2

Cysteine concentration as a function of the %-diafiltration

| | Weight (g) | Protein (%) | Cysteine (%) |
|---|---|---|---|
| Hydrolysate | 172 | 71.5 | 2.1 |
| 100% diafiltered permeate | 167 | 68.0 | 0.2 |
| 200% diafiltered permeate | 150 | 71.3 | 0.1 |
| Retentate after diafiltration | 75.0 | 71.4 | 4.1 |

EXAMPLE 3

100 lt of a 5% whey protein isolate solution is prepared and then hydrolysed using 2% Acid Protease from Enzyme Development Corporation. The solution was hydrolysed for 12 hours at pH 3.0. The reaction was stopped by heating the solution to 80° C. for 30 minutes. Hereafter, the solution was ultrafiltered on a pilot UF unit using Koch HFK 328 membrane having a NMW cut off of 5000 dalton. The hydrolysate was split in two parts. One part was filtered at the pH as is (3.8). The pH of the other part was first raised to 7.0 using sodium hydroxide after which it was ultrafiltered.

Cysteine concentration was measured as a function of the pH during ultrafiltration (table 3).

TABLE 3

Cysteine concentration as a function of the pH during ultrafiltration

| Sample | Cysteine on dry matter |
|---|---|
| Hydrolysate | 3.14 |
| Retentate UF pH 3.9 | 7.73 |
| Retentate UF pH 7.0 | 8.14 |

EXAMPLE 4

The hydrolysate as in example 3 was nanofiltered using the Celgard NF-PES-10 membrane having a NMW cut off of approximately 500 dalton.

The NF-conditions were:

| | |
|---|---|
| Pressure | 30 bar |
| Temperature | 50–55° C. |
| Initial flux | 58 ltrs/m$^2$/hr |
| End flux | 23 ltrs/m$^2$/hr |
| Process | concentrated to 30 ltrs and then 200% diafiltration |

The resulting peptides in the retentate contained 12.9% Cysteine and 3.1% Glycine.

EXAMPLE 5

HPLC specific for Cys Peptides

A Reversed Phase HPLC-method (RPC) was set-up to identify and quantitate cysteine containing peptides in a mixture of peptides. The cysteine residues were first labelled with a fluorescent label (SBD-F; 7-fluorobenzo-2-oxa-1,3-diazole-4-sulfonic acid; Sigma F-4383). This label specifically binds to cysteine residues.

In total 300 μl sample (100 μg protein per ml), 600 μl incubationbuffer (250 mM borate buffer, pH 8, 5 mM EDTA), 300 μl fluorescent probe (0.1% (W/V) in water), 297 μl H$_2$O and 3 μl TBP (tributylfosfine, Fluka) are pipetted in a vial. The vial is capped, the mixture mixed well and incubated at 60C. for 10 minutes. The final concentration of the sample is 0.02 mg/ml.

Hereafter the mixture is cooled to room temperature by putting on ice. Solution is filtered using 0.45 μm PVDF filter (millipore, Millex-HV).

The filtered solutions are analysed by reversed phase chromatography using a Widepore C18 5 μm RPC column (Baker). The binding buffer consisted of demineralized water/0.1% TFA (trifluorazijnzuur) and the peptides were eluted using a acetonitril/0.083% TFA buffer (buffer B). The level of Buffer B was increased to 60% in 90 minutes, whereafter tightly bound material was removed by running 100% buffer for 20 minutes. The injection volume was 150 μl sample.

Figure 1B:
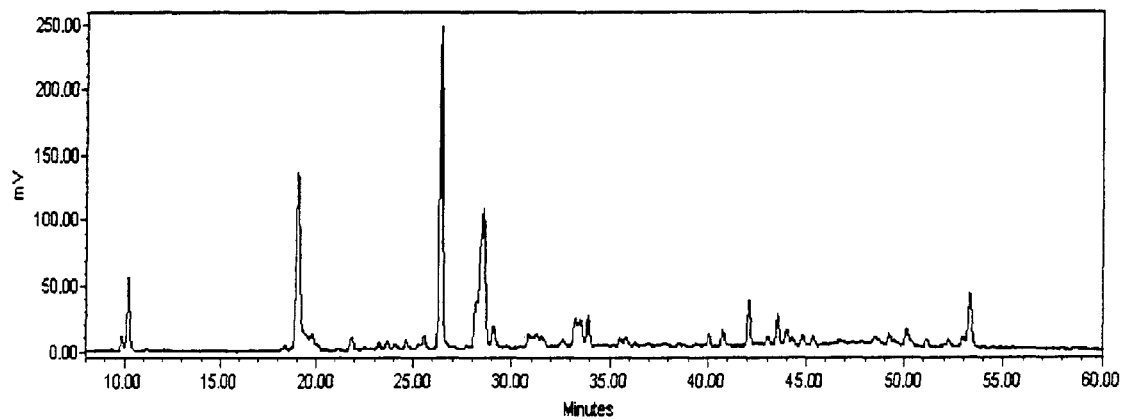

The peptides are detected by measuring absorption at 214 nm and fluorescence (excitation and emission wavelengths respectively 386 nm and 514 nm), see FIG. 1.

Upper panel of FIG. 1 shows the hydrolysate from example 1 before separation detecting the peptides by measuring adsorption at 214 nm Lower panel shows the same hydrolysate detecting specific cysteine containing peptides measuring the fluorescence.

EXAMPLE 6

The cysteine and glycine rich peptides can be used in clinical enteral nutrition formulas. A recipe for such formula is as follows:

| | |
|---|---|
| Cys and Gly rich peptides | 5.00% |
| Calcium Caseinate (DMV International) | 1.96% |
| Malto dextrin DE-20 | 14.0% |
| Emulsifyer (Sternphil E60; Stern) | 0.30% |
| Oil-mix (50% sunflower; 20% MCT; 30% soy-oil) | 4.90% |
| Sodium Chloride | 0.09% |
| Tri-Calcium Phosphate | 0.95% |
| Magnesium Chloride | 0.15% |
| Calcium di-Hydrogen Phosphate | 0.13% |
| Tri-Sodium Citrate | 0.086% |
| Water | 77.99% |
| Total | 100% |

Caseinate is dissolved in part of the deminerilised water at 60° C.; emulsifier is dissolved in the oil-mix; salts are dissolved in 75 ml water. Hereafter, the oil mix, salt, malto dextrin solution and residual water are subsequently mixed in the caseinate solution. This mixture is homogenised twice at 350 bar and at 70° C.

The Cysteine & Glycine rich peptides are then dissolved in the emulsion. The pH is adjusted to 7.0–7.1 using sodium hydroxyde and then the product is retort sterilised for 10 minutes at 121° C.

EXAMPLE 7

The peptides can be used in Infant formula's. A model recipe is as follows:

| Component | Concentration (g/lt) |
|---|---|
| Cys and Gly rich peptides | 10.0 |
| WE80BG (whey protein hydrolysate DMV International) | 10.0 |
| Edible Lactose (DMV International) | 30.0 |
| Malto dextrin DE-20 | 23.0 |
| Corn Syrup Solids | 25.0 |
| Emulsifier (Sternphil E60; Stern) | 5.0 |
| Oil-mix (45% sunflower; 25% MCT; 30% soy-oil) | 40.0 |
| Calcium ortho phosphate | 1.8 |
| Calcium carbonate | 1.3 |
| Magnesium Chloride | 0.3 |
| Potassium Chloride | 0.4 |
| Tri-Sodium Citrate | 0.5 |
| Water | 852.7 |
| Total | 1000 |

The emulsifier is dissolved in the oil fraction. The peptides and carbohydrates are dissolved in part of the water of 70° C. Minerals are dissolved separately. The oil mixture in then added to the peptide/carbohydrate solution and mixed using a high shear mixer for 3 minutes.

The pre-emulsion is then homogenised twice at 250 bars. The formula can either be pasteurised by heating at 80° C. for 15 minutes and spray dried (powdered formula), or sterilised in bottles at 120° C. for 10 minutes (liquid formula).

EXAMPLE 8

The peptides can be incorporated in an instant drink mix. The recipe contains:

| | |
|---|---|
| Cys and Gly rich peptides | 15.00% |
| Whey protein concentrate 80 (Esprion 580; DMV International) | 65.00% |
| Glutamine Peptides (WGE80GPU; DMV International) | 10.00% |
| Vitamin mix (Roche) | 4.90% |
| Cocoa powder (D-11-S, ADM Cocoa, The Netherlands) | 3.00% |
| Flavour; Vanilla JSH00712F, McCormick & Co. | 1.15% |
| Flavour; Chocolate fudge FF22034, McCormick & Co. | 0.95% |
| Sweetener (Aspartame, Nutrasweet) | 0.20% |
| Total | 100% |

The dry ingredient are mixed and then added to 118 ml water. The solution is mixed so that the components dissolve. One serving contains 35 g of powder mix supplying approximately 500 mg Cysteine and 150 mg Glycine.

What is claimed is:

1. A method for the preparation of a mixture of peptides having a cysteine content between 7–20 w/w % from a protein source, comprising one or more cysteine-containing proteins, comprising:
   a) cleaving the cysteine-containing protein of the protein source into peptides;
   b) digesting the peptides by at least one exopeptidase, wherein the exopeptidase is at least attenuated at a cysteine in the peptide; and
   c) purifying the digested peptides.

2. A method for the preparation of a mixture of peptides having a total cysteine and glycine content of 7–20 w/w % from a protein source, comprising one or more cysteine-containing and glycine-containing proteins, comprising:
   a) cleaving the cysteine-containing and glycine-containing protein into peptides;
   b) digesting the peptides by at least one exopeptidase, wherein the exopeptidase is at least attenuated at a cysteine or a glycine in the peptide and
   c) purifying the digested peptides.

3. The method according to claim 1 further comprising performing step a) and step b) simultaneously.

4. The method according to claim 1, wherein the at least one exopeptidse comprises carboxypeptidase Y.

5. The method according to claim 1, wherein the protein source comprises at least two different cysteine-containing proteins.

6. The method according to claim 1, wherein the protein source comprises at least two different proteins, wherein at least one protein contains at least one cysteine residue and at least one protein contains at least one glycine residue.

7. The method according to claim 1, wherein the protein source consists of edible proteins.

8. The method according to claim 1, wherein the protein source comprises whey protein isolate, whey protein concentrate, or combinations thereof.

9. The method according to claim 1, wherein the protein source comprises one or more proteins selected from the group consisting of albumin, α-lactalbumin, bovine serum albumin, wheat gluten, maize protein isolate, egg proteins, ovalbumin, and cystain.

10. The method according to claim 1, wherein sulfur bridges between cysteine residues in the protein source are kept intact during step a) and step b).

11. The method according to claim 10, wherein step a) and step b) are performed at a pH of 2–8.

12. The method according to claim 1, wherein an endopeptidase is used in the cleavage step a).

13. The method according to claim 1, wherein an enzyme with both endopeptidase and exopeptidase activities is used in the cleavage step a), and wherein the exopeptidase activity is attenuated at a cysteine or glvcine.

14. The method according to claim 13, wherein the exopeptidase activity of the enzyme is attenuated at a cysteine.

15. The method according to claim 13, wherein the enzyme is selected from the group consisting of a protease from *Asyergillus orvzae*, Acid Protease A (Protease from *Aspergilus niger*), Protease 2A (Protease from *Aspergillus niger*), Protase B (fungal protease), a protease from *Aspergillus soja*, and Acid Protease (acid protease from *Rhizopus niveus*).

16. The method according to claim 2, further comprising performing step a) and step b) simultaneously.

17. The method according to claim 2, wherein the at least one exopeptidase comprises carboxypeptidase.

18. The method according to claim 2, wherein the protein source comprises at least two different cysteine-containing proteins.

19. The method according to claim 2, wherein the protein source comprises at least two different proteins, wherein at least one protein contains at least one cysteine residue and at least one protein contains at least one glycine residue.

20. The method according to claim 2, wherein the protein source comprises edible proteins.

21. The method according to claim 2, wherein the protein source comprises whey protein isolate, whey protein concentrate, or combinations thereof.

22. The method according to claim 2, wherein the protein source comprises one or more proteins selected from the group consisting of albumin, a-lactalbumin, bovine serum albumin, wheat gluten, maize protein isolate, egg proteins, ovalbumin, and cystatin.

23. The method according to claim 2, wherein sulfur bridges between cysteine residues in the protein source are kept intact during step a) and step b).

24. The method according to claim 23, wherein step a) and step b) are performed at a pH of 2–8.

25. The method according to claim 2, wherein an endoptidase is used in the cleavage step a).

26. The method according to claim 2, wherein an enzyme with both endopeptidase and exopeptidase activities is used in the cleavage step a), and wherein the exopeptidase activity is attenuated at a cysteine or glycine.

27. The method according to claim 26, wherein the exopeptidase activity of the enzyme is attenuated at a cysteine.

28. The method according to claim 26, wherein the enzyme is selected from the group consisting of a protease from *Aspergillus oryzae*, Acid Protease A (Protease from *Aspergillus niger*), Protease 2A (Protease from *Aspergillus niger*), Protase B (fungal protease), a protease from *Aspergillus soja*, and Acid Protease (acid protease from *Rhizopus niveus*).

29. A preparation comprising a mixture of cysteine-rich peptides, which comprise 7–20% w/w cysteine, wherein said peptides have a molecular weight of 5000 Da or more.

30. A preparation comprising a mixture of cysteine-rich peptides, which comprise 7–20 w/w % cysteine, wherein at least 80% of the peptides comprise a terminal cysteine, terminal glycine, or a combination of both.

31. The preparation of claim 30, wherein at least 80% of the peptides comprise a terminal cysteine residue.

32. The preparation of claim 30, wherein at least 80% of the peptides comprise a terminal glycine residue.

33. A food comprising a preparation comprising a mixture of cysteine-rich peptides, which comprise 7–20 w/w % cysteine.

34. The food of claim 33, that is an infant formula.

35. A pharmaceutical composition or medicament comprising a preparation comprising a mixture of cysteine-rich peptides, which comprise 7–20 w/w % cysteine.

36. A composition that is produced by the method of claim 1, comprising a mixture of cysteine-rich peptides, which comprises 7–20 w/w % cysteine.

37. The composition of claim 36, wherein said peptides are obtained from one or more albumin(s).

38. The composition of claim 36, wherein said peptides are obtained from one or more egg protein(s).

39. The composition of claim 36, wherein said peptides are obtained from ore milk protein(s).

40. The composition of claim 36, wherein said peptides are obtained from whey protein.

41. The composition of claim 36, wherein said peptides are obtained from wheat gluten.

42. The composition of claim 36, wherein said peptides are obtained from one or more maize protein(s).

43. A food comprising the composition of claim 36.

44. The food claim 43 that is an infant formula.

45. A pharmaceutical composition or medicament comprising the composition of claim 36.

46. A preparation comprising a mixture of cysteine- and glycine-rich peptides, which comprise 7–20% w/w cysteine and glycine, wherein said peptides have a molecular weight of 5000 Da or more.

47. A preparation comprising a mixture of cysteine- and glycine-rich peptides, which comprise 7–20 w/w % cysteine and glycine, wherein at least 80% of the peptides comprise a terminal cysteine, terminal glycine or a combination of both.

48. The preparation of claim 47, wherein at least 80% of the peptides corn cysteine residue.

49. The preparation of claim 47, wherein at least 80% of the peptides comprise a terminal glycine residue.

50. A food comprising a preparation that comprises a mixture of cysteine and glycine-rich peptides, which corn rise 7–20 w/w % cysteine and glycose.

51. The food of claim 50 that is an infant formula.

52. A pharmaceutical composition or medicament comprising a preparation comprising a mixture of cysteine- and glycine-rich peptides, which comprise 7–20 w/w % cysteine and glycine.

53. A composition that is produced by the method of claim 2, comprising cysteine- and glycine-rich peptides, which comprises 7–20% w/w % cysteine and glycine.

54. The composition of claim 53, wherein said peptides are obtained from one or more albumin(s).

55. The composition of claim 53, wherein said peptides are obtained from one or more egg protein(s).

56. The composition of claim 53, wherein said peptides are obtained from one or more milk protein(s).

57. The composition of claim 53, wherein said peptides are obtained from whey protein.

58. The composition of claim 53, wherein said peptides are obtained from wheat gluten.

59. The composition of claim 53, wherein said peptides are obtained from one or more maize protein(s).

60. A food comprising the composition of claim 53.

61. The food of claim 60, that is an infant formula.

62. A pharmaceutical composition or medicament comprising the composition of claim 53.

* * * * *